United States Patent
Cavaleri

(10) Patent No.: US 9,782,364 B1
(45) Date of Patent: Oct. 10, 2017

(54) CURCUMIN-BASED COMPOSITIONS AND METHODS OF USE THEREOF

(71) Applicant: Franco Cavaleri, Surrey (CA)

(72) Inventor: Franco Cavaleri, Surrey (CA)

( * ) Notice: Subject to any disclaimer, the term of this patent is extended or adjusted under 35 U.S.C. 154(b) by 0 days.

(21) Appl. No.: 15/236,443

(22) Filed: Aug. 14, 2016

Related U.S. Application Data

(60) Provisional application No. 62/249,384, filed on Nov. 2, 2015.

(51) Int. Cl.
*A61K 31/56* (2006.01)
*A61K 31/12* (2006.01)
*A61K 31/573* (2006.01)
*G01N 33/50* (2006.01)

(52) U.S. Cl.
CPC ............ *A61K 31/12* (2013.01); *A61K 31/573* (2013.01); *C12Y 207/11001* (2013.01); *G01N 33/5014* (2013.01); *G01N 2333/912* (2013.01)

(58) Field of Classification Search
CPC ................................ A61K 31/57; A61K 31/12
USPC .................................................. 514/171.679
See application file for complete search history.

(56) References Cited

U.S. PATENT DOCUMENTS

| | | | |
|---|---|---|---|
| 8,058,314 B2* | 11/2011 | Caplan ................. | A61K 9/0073 514/456 |
| 2014/0128337 A1* | 5/2014 | Barthomeuf ......... | A61K 31/704 514/34 |
| 2014/0142168 A1* | 5/2014 | Barthomeuf ........... | A61K 31/12 514/449 |

* cited by examiner

Primary Examiner — Raymond Henley, III

(57) ABSTRACT

Methods for reducing MSK1 levels in a plurality of cells are disclosed. For example, the methods include providing to the cells a curcumin composition that is at least 5% curcumin III. Methods for inhibiting MSK1 serine$^{376}$ phosphorylation in a plurality of cells are also disclosed, which include providing to the cells a curcumin composition that is at least 5% curcumin III. In addition, methods for ameliorating inflammation in a subject are disclosed, which include providing to a subject a curcumin composition that is at least 5% curcumin III. Still further, methods for ameliorating symptoms in a subject having glucocorticoid-resistant inflammatory disease are disclosed, which include providing to a subject a curcumin composition that is at least 5% curcumin III. In addition, compositions are disclosed that include a curcumin composition consisting of at least 5% curcumin III; glucocorticoids; and a pharmaceutically acceptable solvent, filler, or carrier.

19 Claims, 10 Drawing Sheets

CURCUMIN-BASED COMPOSITIONS AND METHODS OF USE THEREOF

CROSS-REFERENCE TO RELATED APPLICATIONS

This application claims priority to, and incorporates by reference, U.S. provisional patent application Ser. No. 62/249,384, filed Nov. 2, 2015.

FIELD OF THE INVENTION

The field of the present invention relates to certain curcumin-containing compositions and methods of use thereof, which can be used to modulate MSK1 production and ameliorate a variety of health conditions.

BACKGROUND OF THE INVENTION

The health benefits of curcumin are known and have been demonstrated by researchers in recent years. However, several challenges continue to exist, with respect to the formulation of curcumin-based pharmaceuticals and dietary supplements. More specifically, the most common source of curcumin, the Indian spice turmeric (a member of Zingiberaceae), does not contain a sufficient amount of curcumin to provide an efficacious dose to a person. In fact, the therapeutic benefits provided by natural curcumin extracts have been relatively modest, inconsistent, and not well understood. Accordingly, there is a continuing need for improved curcumin-based formulations, which address these current challenges.

The present invention, as described further below, addresses many of the foregoing challenges.

SUMMARY OF THE INVENTION

According to certain aspects of the present invention, methods for inhibiting the production of MSK1 in a plurality of cells are disclosed (or otherwise reducing the levels of MSK1 in a plurality of cells). In certain embodiments, the methods include providing to the cells an effective amount of a curcumin composition that is at least 5% (w/v) curcumin III or, preferably, at least 30% (w/v) curcumin III or, more preferably, at least 50% (w/v) curcumin III or, even more preferably, at least 70% (w/v) curcumin III, such as at least 90% (w/v) curcumin III.

According to additional aspects of the present invention, methods for inhibiting MSK1 serine$^{376}$ phosphorylation in a plurality of cells are disclosed. Such methods generally include providing to the cells an effective amount of a curcumin composition that is at least 5% curcumin III or, preferably, at least 30% (w/v) curcumin III or, more preferably, at least 50% (w/v) curcumin III or, even more preferably, at least 70% (w/v) curcumin III, such as at least 90% (w/v) curcumin III.

According to further aspects of the present invention, methods for ameliorating inflammation in a subject are disclosed. The methods generally include providing to a subject a curcumin III enriched composition that is described herein.

According to yet further aspects of the present invention, methods for ameliorating symptoms in a subject having glucocorticoid-resistant inflammatory disease are disclosed, which include providing to a subject a curcumin III enriched composition that is described herein.

According to still further aspects of the present invention, therapeutic compositions are disclosed that include a curcumin composition consisting of at least 5% curcumin III; one or more glucocorticoids; and a pharmaceutically acceptable solvent, filler, or carrier.

In the foregoing aspects of the invention, while the curcumin composition employed may comprise 5% curcumin III, in certain preferred embodiments, the curcumin composition employed may comprise at least 30% curcumin III. Still more preferably, the invention provides that the curcumin composition may comprise at least 50% curcumin III, at least 70% curcumin III or, even more preferably, at least 90% curcumin III.

The above-mentioned and additional features of the present invention are further illustrated in the Detailed Description contained herein.

DETAILED DESCRIPTION OF THE INVENTION

Figure 1:
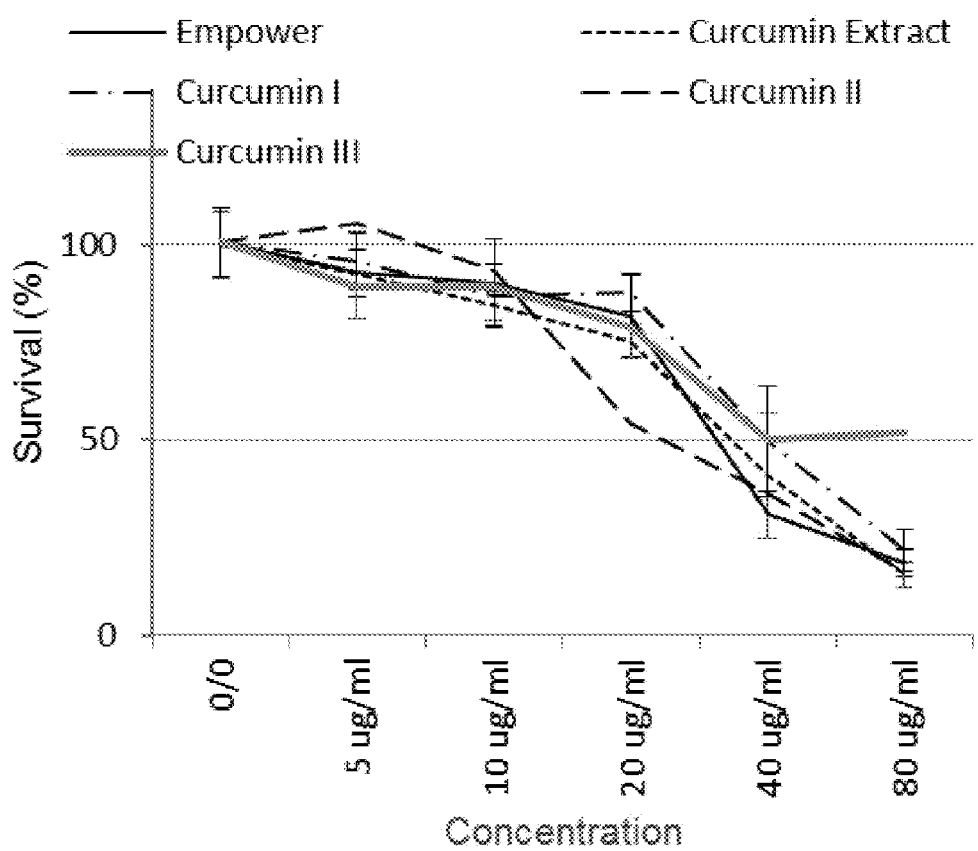
FIG. 1: MTT assay results demonstrating HEK293 cell survival of approximately 80% for all three curcuminoids (ranging from 20 to 22 µg/mL of the applicable curcuminoid).

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain preferred embodiments, the present invention includes certain curcumin-containing and curcumin-enriched compositions (and methods of using such compositions). More particularly, the present invention includes certain compositions that contain elevated and concentrated levels of curcumin III (relative to the amount of curcumin III found in natural curcumin extract), which can be used to inhibit MSK1 production (or otherwise reduce MSK1 levels), inhibit MSK1 serine$^{376}$ phosphorylation, and ameliorate a variety of associated health conditions and/or impart one or more associated health benefits.

Mitogen- and stress-activated protein kinase 1 (MSK1) is a nuclear kinase that plays a significant role in transcription regulation. As described below, the invention provides that curcumin III (and not curcuminoids I and II) can be used to selectively and efficaciously inhibit cytoplasmic and nuclear MSK1 production, inhibit MSK1 serine$^{376}$ phosphorylation, and counteract the recruitment of MSK1 at inflammatory gene promotors. The curcumin III compositions described herein—and related methods of using such compositions—provide a major step in the transactivation regulation of downstream transcription factors that are key to cell survival and recruitment of inflammatory and immune system events. For example, as demonstrated in the Examples below, the ability of the curcumin III compositions described herein to inhibit MSK1 production (or otherwise significantly reduce MSK1 levels), indicates that such compositions may also (indirectly) be used to modulate NFkB (nuclear factor kappa-light-chain-enhancer of activated B cells)—the aberrant expression of which has been linked to cancer, inflammation, and autoimmune diseases. The curcumin III compositions (and related methods) of the present invention provide improved efficacy, reliability, and drug target selectivity, relative to natural curcumin extracts.

A natural curcumin extract comprises a mixture of curcumin I, desmethoxycurcumin (curcumin II), and bisdemethoxycurcumin (curcumin III). The term curcumin refers to the principal curcuminoid in the Indian spice turmeric plant (a member of Zingiberaceae). The IUPAC name for the curcumin I molecule is (1E,6E)-1,7-Bis(4-hydroxy-3-methoxyphenyl)-1,6-heptadiene-3,5-dione. Although curcumin I may exist in several different tautomeric forms, the enol form is illustrated below:

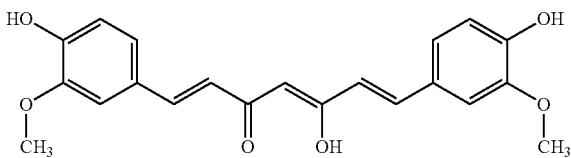 [SMILES: COc1cc(/C=C/C(=O)/C=C(O)/C=C/c2ccc(O)c(OC)c2)ccc1O]

The IUPAC name for the desmethoxycurcumin (curcumin II) molecule is (1E,6E)-1-(4-Hydroxy-3-methoxyphenyl)-7-(4-hydroxyphenyl)hepta-1,6-diene-3,5-dione, and has the chemical structure shown below:

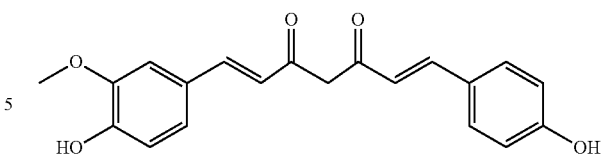

The IUPAC name for bis-desmethoxycurcumin (curcumin III) that is used in the compositions and methods of the present invention is (1E,6E)-1,7-bis(4-hydroxyphenyl)hepta-1,6-diene-3,5-dione, and has the chemical structure shown below:

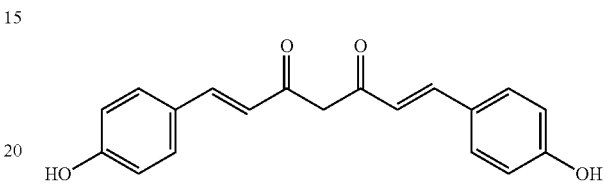

According to certain preferred embodiments, the invention provides that curcumin III may be extracted from turmeric plant rhizome (*Curcuma longa*) and subsequently concentrated to the desired level. Alternatively, the invention provides that the curcumin III molecule may be chemically synthesized and added to a natural curcumin extract (or the synthesized curcumin III molecule may be used as the sole source of the curcumin III composition described herein). As explained below, the desired concentration may be at least 5%, 30%, 50%, 70%, or 90% (w/v) curcumin III.

According to certain preferred embodiments of the present invention, methods for inhibiting the production of MSK1 in a plurality of cells are provided (or otherwise reducing MSK1 levels in a plurality of cells). In such embodiments, the methods include providing to the cells (or administering to a biological system that comprises a plurality of cells) an effective amount of a curcumin composition that is at least 5% curcumin III. According to additional preferred embodiments of the present invention, methods for inhibiting MSK1 serine$^{376}$ phosphorylation in a plurality of cells are provided. Such methods include providing to the cells (or administering to a biological system that comprises a plurality of cells) an effective amount of a curcumin composition that is at least 5% curcumin III. According to further related embodiments of the present invention, methods for ameliorating inflammation in a subject are provided, which generally include providing to a subject an effective amount of a curcumin composition that is at least 5% curcumin III. In these embodiments, the concentration of the curcumin III composition may be enhanced to increase efficacy, such as by providing to the cells (or administering to a biological system that comprises a plurality of cells) a curcumin composition that is at least 5%, 30%, 50%, 70%, or 90% (w/v) curcumin III. The "effective amount" of such curcumin III composition will preferably be sufficient to significantly reduce the amount of MSK1 protein being expressed in the target cells. For example, the "effective amount" of such curcumin III composition will preferably be sufficient to reduce the amount of MSK1 protein being expressed in the target cells by at least 25% relative to a control (i.e., cells which do not receive the curcumin III composition) or, more preferably, by at least 50% relative to a control.

According to yet further preferred embodiments of the present invention, methods for ameliorating symptoms in a subject having an adverse medical condition in which MSK1 is implicated are provided, including glucocorticoid-resistant inflammatory diseases and chemotherapy-resistant cancers. In such embodiments, the methods include providing to a subject a curcumin composition that is at least 5% curcumin III (or, alternatively, at least 30%, 50%, 70%, or 90% (w/v) curcumin III). According to certain related embodiments of the present invention, therapeutic compositions are provided that include a curcumin composition consisting of at least 5% curcumin III; glucocorticoids; and a pharmaceutically acceptable solvent, filler, or carrier. As used herein, "glucocorticoids" refers to certain steroid hormones that are known to bind to glucocorticoid receptors (RCEs). Non-limiting examples of glucocorticoids include: cortisol, cortisone, prednisone, prednisolone, methylprednisolone, dexamethasone, betamethasone, triamcinolone, beclometasone, fludrocortisone, deoxycorticosterone, and aldosterone.

In the foregoing embodiments of the invention, while the curcumin composition employed may comprise 5% curcumin III, in certain preferred embodiments, the curcumin composition employed may comprise at least 30% curcumin III. Still more preferably, the invention provides that the curcumin composition may comprise at least 50% curcumin III, at least 70% curcumin III or, even more preferably, at least 90% curcumin III—depending on the desired potency.

The invention provides that the concentrated forms of the curcumin III based compositions (and methods of using such compositions) described herein exhibit many benefits—for humans, canines, cats and equine. First, as demonstrated below and described herein, the invention provides that elevated levels of curcumin III will selectively inhibit MSK1 production, thereby producing anti-inflammatory activity. In addition, the invention provides that the compositions and methods described herein may be used for therapeutic nutrition; anti-inflammatory therapy for autoimmune disease and other chronic and acute inflammatory ailments; treatment of pain, swelling and inflammation; nutritional supplementation; superbug treatments; and antimicrobial, antifungal, antibacterial, and antiviral therapies.

In certain specific embodiments, the compositions and methods described herein may be used to ameliorate the effects of autoimmune diseases (and other inflammatory conditions), such as rheumatoid arthritis, colitis, non-specific inflammatory bowel diseases, crohn's disease, lupus, multiple sclerosis, psoriasis, type-I diabetes, diabetes, myocarditis, thyroiditis, uveitis, systemic lupus erythromatosis, myasthenia and gravis. Furthermore, the compositions and methods described herein may be used to ameliorate the effects of autoimmune syndromes, such as the sources of immune-mediated inflammation (which can promote chronic inflammation, Alzheimer's, asthma, allergies, obesity, chronic fatigue, fibromyelia, premature aging, and general memory impediments). Still further, the compositions and methods may be used for the purpose of performance enhancement; recovery from physical exercise; and to help neutralize lactic acid, oxidation and associated inflammatory responses to workload to improve recovery rate, anabolism, reduce post-workout soreness and associated fatigue (and allow for repeat workout sessions earlier than could otherwise be executed in typical workout and training cycles).

The invention provides that the compositions described herein may be administered in any desired and effective manner, e.g., as pharmaceutical compositions or nutritional supplements for oral ingestion. More particularly, for example, pharmaceutically acceptable compositions or nutritional supplements of the invention may comprise one or more of the compositions described herein with one or more acceptable carriers. Regardless of the route of administration selected, the compositions may be formulated into acceptable dosage forms by conventional methods known to those of skill in the art. For example, acceptable carriers include, but are not limited to, sugars (e.g., lactose, sucrose, mannitol, and sorbitol), silicon dioxide, starches, cellulose preparations (such as microcrystalline cellulose), calcium phosphates (e.g., dicalcium phosphate, tricalcium phosphate and calcium hydrogen phosphate), sodium citrate, water, aqueous solutions, alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes, paraffins, silicones, talc, silicylate, etc.

Each acceptable carrier used in a pharmaceutical composition or nutritional supplement of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions and nutritional supplements of the invention may, optionally, contain additional ingredients and/or materials commonly used in pharmaceutical compositions and/or nutritional supplements. Such ingredients and materials include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxy methyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; (28) vitamins and minerals; (29) proteins that carry therapeutic or nutritional benefits, such as whey protein and other milk-derived proteins; and (30) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions and nutritional supplements suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, or a paste. These formulations may be prepared by methods known in the art, e.g., by means of conventional pan-coating, mixing, granulation or lyophilization processes.

Solid dosage forms for oral administration (capsules, tablets, pills, powders, granules and the like) may be prepared by mixing the active ingredient(s) with one or more acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the art. The tablets, and other solid dosage forms, may also be formulated so as to provide slow or controlled release of the active ingredient therein. They may be sterilized by, for example, filtration through a bacteria-retaining filter. These compositions may also optionally contain opacifying agents that release the active ingredient only, or preferentially, in a certain portion of the gastrointestinal tract, optionally, in a delayed manner. The active ingredient can also be in a microencapsulated form.

Liquid dosage forms for oral administration include acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

EXAMPLES

The following Examples demonstrate the effects of curcumin III on cytoplasmic and nuclear MSK1 expression, as well as the effects of curcumins I, II, and III on cytoplasmic and nuclear MSK1 serine$^{376}$ phosphorylation.

Example 1—MTT Assay

MTT (3-[4,5-dimethylthiazol-2-yl]-2,5-diphenyltetrazolium bromide) Assays are Routinely Used to Measure Cell Viability and Survival In this Example, cytotoxicity of curcuminoids on two cell types—HEK293T and BV2 microglia—was measured. The MTT assay quantifies the formazan production by live cells from the tetrazolium ring cleavage of MTT. Reduction of MTT is directly proportional to metabolic activity and therefore relatable to cell viability and survival. A first MTT assay was performed on HEK293T cells in a 96-well plate requiring $3 \times 10^4$ cells per well. The MTT assay was also performed using BV2 microglia cells, pursuant to the same protocol (utilizing a 96-well plate requiring $3 \times 10^4$ cells per well). Dimethyl sulfoxide (DMSO) was used in the test drug (curcuminoid) preparation at 0.2%. The MTT assay was used to measure the health of the cells in culture with various treatment concentrations of various curcumin preparations.

Figure 2:
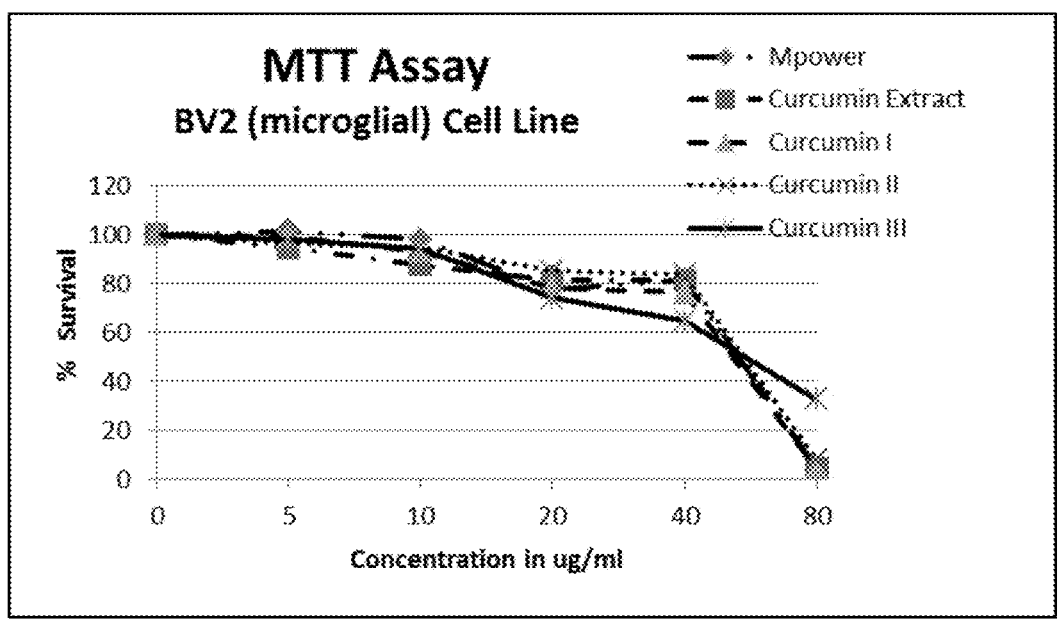
FIG. 2: MTT assay results demonstrating BV2 cell survival of approximately 80% for all three curcuminoids (ranging from 20 to 22 µg/mL of the applicable curcuminoid).

As shown in FIG. 1 (HEK293T cells) and FIG. 2 (BV2 microglia), the MTT assay results revealed that the selected cell models are relatively resilient to the curcuminoid drugs at the tested concentrations. Cell survival was shown to begin to decline below 80% survival at a drug (curcuminoid) concentration around 40 µg/ml. Accordingly, a final test concentration of 22 µg/ml was selected and employed in the Examples that follow.

Example 2—Western Blot Analysis of Cytoplasmic and Nuclear Cell Fractions

Western blot analysis was performed in multiple varying formats before optimization was achieved. The BV2 microglia cell line was cultured in Dulbecco's Modified Eagle's Medium (DMEM)—complete medium. The complete medium consisted of DMEM, 1% Ampicillin, and 10% Fetal Bovine Serum (FBS). BV2 microglia cells, at a cell count of approximately $2 \times 10^6$, were seeded in each well (6 wells per plate) with 2.0 ml complete medium and cultured overnight in a ThermaForma HepaFilter Series II Co$_e$ Incubator at 37° Celsius. Upon establishing confluence, subconfluent cells were washed out and the wells were prepared with drug pre-treatment after overnight incubation.

The test drugs (curcuminoids) were procured as follows: curcumin I research standard (03926) (ChromaDex Irvine, Calif. USA) (97.7% purity); curcumin II research standard (04230) (ChromaDex Irvine, Calif. USA) (97.3%); curcumin III research standard (B6938) (Sigma-Aldrich St. Louis, Mo., USA) (97.7% purity); curcumin extract (curcumin I—77.7%, curcumin II—16.9%, curcumin III—0.9%) research standard (03928) (ChromaDex Irvine, Calif. USA) (95.3% purity); and Lipopolysaccharide (LPS) from *E. Coli* (L2630) (Sigma-Aldrich St. Louis, Mo., USA).

Curcuminoids are not soluble in aqueous medium due to their hydrophobic characteristic. However, curcuminoid extracts are soluble in polar organic solvents, such as DMSO and acetone. In this Example, each curcuminoid preparation was first dissolved in DMSO. DMSO was used in the drug preparation at 0.2%. The drug/DMSO solution was subsequently dissolved in DMEM to achieve a final drug concentration for each curcuminoid preparation tested—22.0 µg/ml curcuminoid. The DMEM/drug solution was used to replace the culture DMEM well medium and incubated for 30 minutes at 37-degrees Celsius in a ThermaForma incubator. At 31 minutes, lipopolysaccharide (LPS at 1.0 µl/ml final well concentration) induction of the cells was executed, except for the DMSO-only well to stimulate cell response amidst drug pre-treatment and without drug treatment.

The plates were then incubated for another 30 minutes after LPS stimulation. Upon removal from incubation, the cell medium was carefully removed and cells were washed, scraped, and collected with phosphate-buffered saline (PBS). Using a ThermoFisher Scientific NE-PER Nuclear and Cytoplasmic Extraction Kit (obtained from Thermo-Fisher Scientific Burlington, Ontario Canada), the cells were lysed and the cytoplasmic and nuclear protein fractions were collected and separated with the intention of probing each fraction for subcellular changes in cytoplasmic and nuclear proteins (as described further below).

Total protein concentration for each fraction was determined using a Bio Rad Protein Assay that is based on the Bradford Assay (dye-binding method). The total protein concentration determination was made prior to test sample preparation for gel electrophoresis execution (described below). The protein concentration colorimetric assay kit was purchased from Bio Rad Laboratories Canada Ltd. (Montreal, Quebec Canada). Each test sample was then prepared for loading and subjected to gel electrophoresis (SDS-PAGE) using a BioRad stain free gel system (Catalog No. 161-0181) and subsequently transferred/blotted to a nitrocellulose membrane (ThermoFisher Scientific Product No. 88018), blocked, and prepared for primary antibody treatment for each target.

The targets analyzed in the Western Blot included NFkB-p65 and its nucleocytoplasmic translocation, as well as kinases (including MSK1) and their covalent modifications upstream of and involved in the regulation of NFkB. Antibodies against NFkB-p65 (Ab16502) were procured from Abcam Inc. (Toronto, Ontario, Canada) as a primary antibody to probe for total NFkB-p65 levels in both nuclear and cytoplasmic fractions. Antibodies against phosphorylated NFkB p65 at serine 276 (sc-101749) were procured from Santa Cruz Biotechnologies Inc. Antibodies against MSK1 total protein (SAB4503597) were procured from Sigma-Aldrich Company (St. Louis, Mo., USA), and antibodies against phosphorylated MSK1 at serine 376 (SAB4504475) were also procured from Sigma-Aldrich Company. The antibodies were used to probe for both nuclear and cytoplasmic levels of each protein and its modified state—the phosphorylation site which determines its activated (or most active) state. Secondary antibody conjugated to a horseradish peroxidase (HRPO) enzyme was used to detect the bound primary antibodies. Following incubation, washing, and substrate activation of the HRPO-labeled secondary antibody, the membrane was scanned using a Bio Rad ChemDoc MP Imaging System (and the detected Western Blot bands were quantified using Image J Software).

Figure 3:
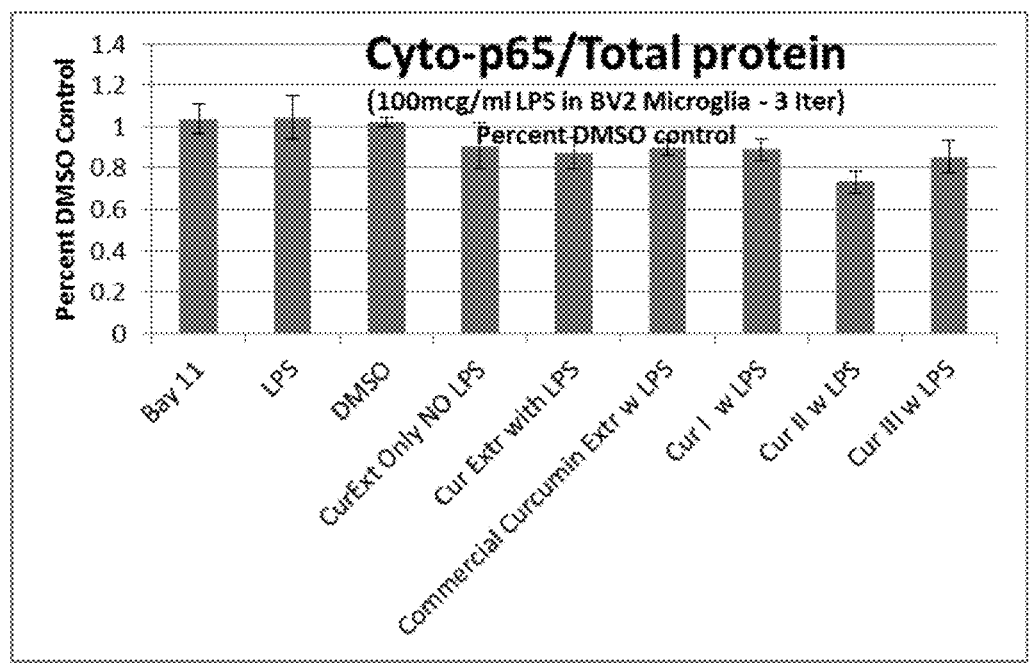
FIG. 3: measurements of cytoplasmic NFkB-p65 protein levels relative to total protein concentration in BV2 cell lines provided with curcumin extract, curcuminoid I, curcuminoid II, curcuminoid III, and controls.
Figure 4:
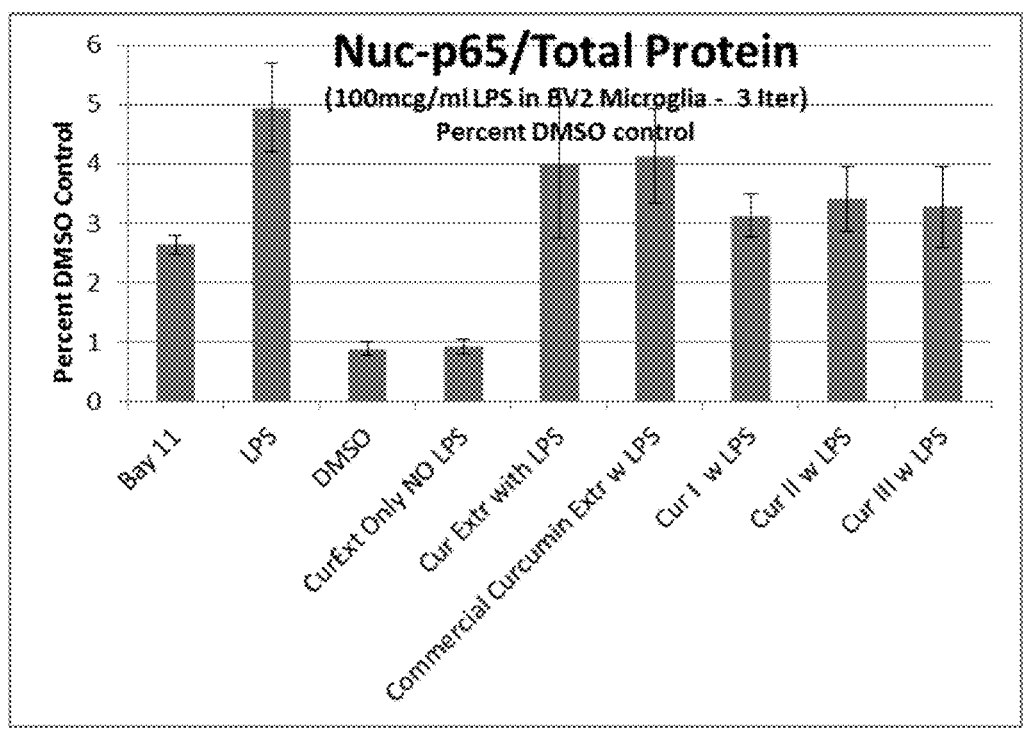
FIG. 4: measurements of nuclear NFkB-p65 protein levels relative to total protein concentration in BV2 cell lines provided with curcumin extract, curcuminoid I, curcuminoid II, curcuminoid III, and controls.
Figure 5:
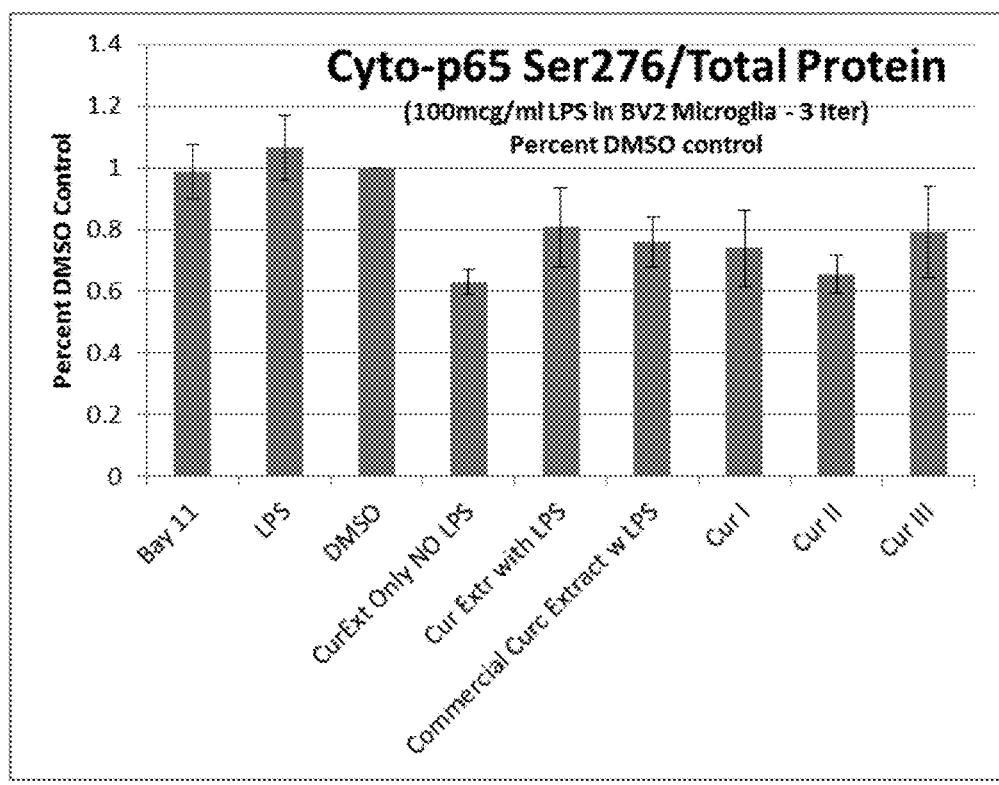
FIG. 5: measurement of cytoplasmic NFkB p65 that is phosphorylated at the serine 276 phosphosite, relative to total protein concentration in BV2 cell lines provided with curcumin extract, curcuminoid I, curcuminoid II, curcuminoid III, and controls.
Figure 6:
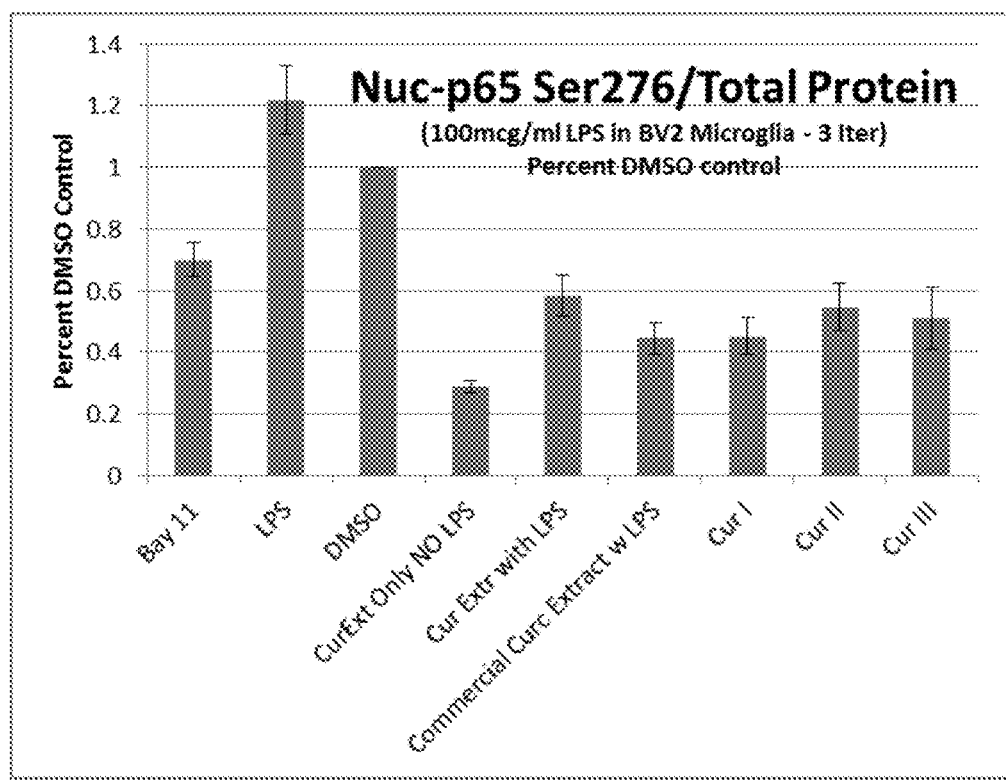
FIG. 6: measurement of nuclear NFkB p65 that is phosphorylated at the serine 276 phosphosite, relative to total protein concentration in BV2 cell lines provided with curcumin extract, curcuminoid I, curcuminoid II, curcuminoid III, and controls.

FIG. 3 shows the Western Blot measurements of cytoplasmic NFkB-p65 protein levels relative to total protein concentration, in BV2 cell lines provided with curcumin extract, curcuminoid I, curcuminoid II, curcuminoid III, and controls. FIG. 4 shows the Western Blot measurements of nuclear NFkB-p65 protein levels relative to total protein concentration, in BV2 cell lines provided with curcumin extract, curcuminoid I, curcuminoid II, curcuminoid III, and controls. FIG. 5 shows the Western Blot measurements of cytoplasmic NFkB-p65 phosphorylated at serine 276 relative to total protein concentration, in BV2 cell lines provided with curcumin extract, curcuminoid I, curcuminoid II, curcuminoid III, and controls. FIG. 6 shows the Western Blot measurements of nuclear NFkB-p65 that is phosphorylated at serine 276 relative to total protein concentration, in BV2 cell lines provided with curcumin extract, curcuminoid I, curcuminoid II, curcuminoid III, and controls.

The cytosolic and nuclear NFkB-p65 data (FIGS. 3 and 4) reveal that nucleotranslocation is not significantly inhibited by curcumin extract, curcumin I, curcumin II, nor curcumin III. As shown in FIGS. 5 and 6, however, curcumin extract and each of the curcuminoids—I, II, and III—moderately inhibit NFkB-p65 serine$^{276}$ phosphorylation to significantly inhibit p65-p50 transactivation, while nucleotranslocation is relatively low in this same context. Indeed, the more robust inhibition of NFkB-p65 serine$^{276}$ phosphorylation of the transcription factor's Transactivation Domain II reveals a relevant mechanism by which each of the curcuminoids inhibits p65p50 transactivation and downstream immune and inflammatory activity. These data show that each curcuminoid, including the curcumin extract, comparably inhibits this key site phosphorylation to downregulate immune system and inflammatory activity. This demonstrates an ability of curcuminoid drugs to treat cells that may feature pathological constitutive p65-p50 nucleotranslocation, which is a common pathological feature of cancer and chronic inflammatory conditions (including autoinflammatory and autoimmune conditions).

Figure 7:
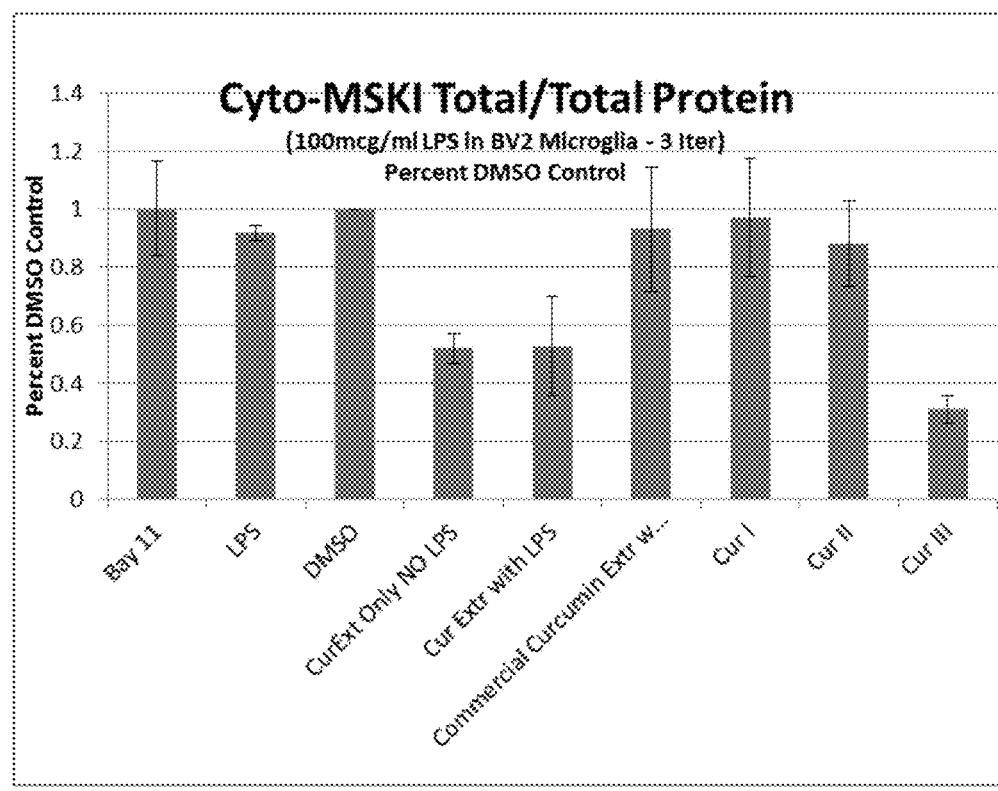
FIG. 7: measurement of cytoplasmic MSK1 protein levels relative to total protein concentration in BV2 cell lines provided with curcumin extract, curcuminoid I, curcuminoid II, curcuminoid III, and controls.
Figure 8:
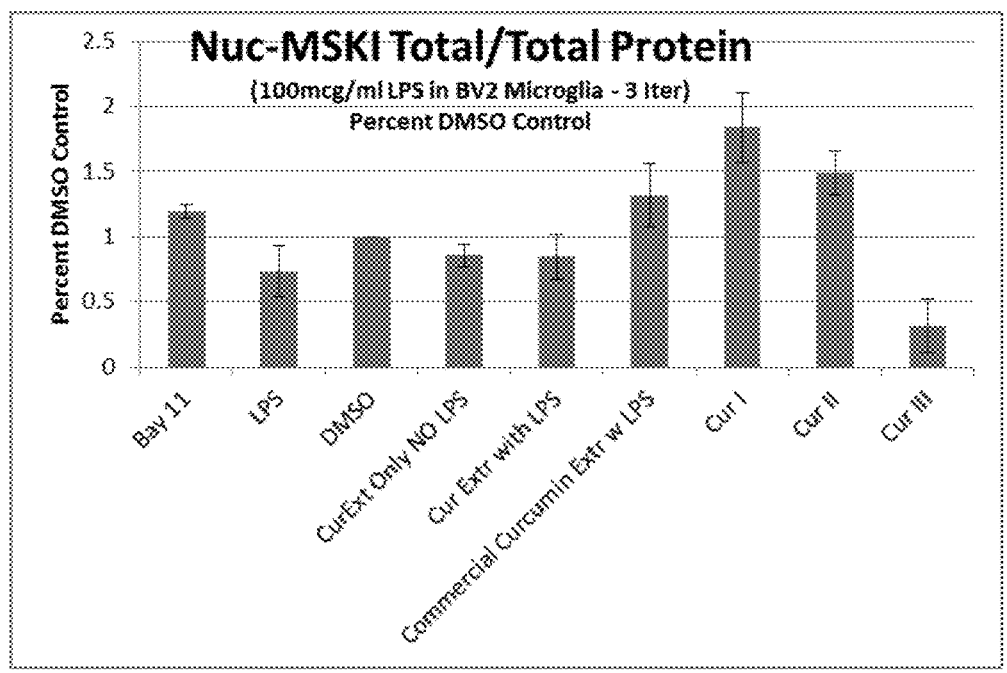
FIG. 8: measurement of nuclear MSK1 protein levels relative to total protein concentration in BV2 cell lines provided with curcumin extract, curcuminoid I, curcuminoid II, curcuminoid III, and controls.
Figure 9:
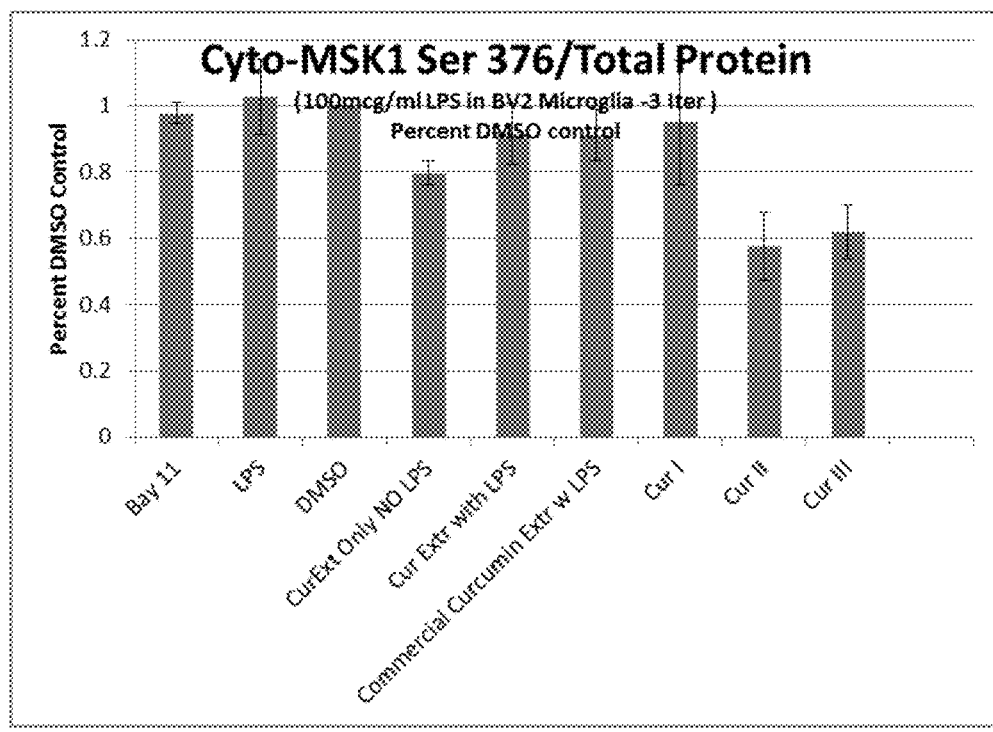
FIG. 9: measurement of cytoplasmic MSK1 that is phosphorylated at the serine 376 phosphosite, relative to total protein concentration in BV2 cell lines provided with curcumin extract, curcuminoid I, curcuminoid II, curcuminoid III, and controls.
Figure 10:
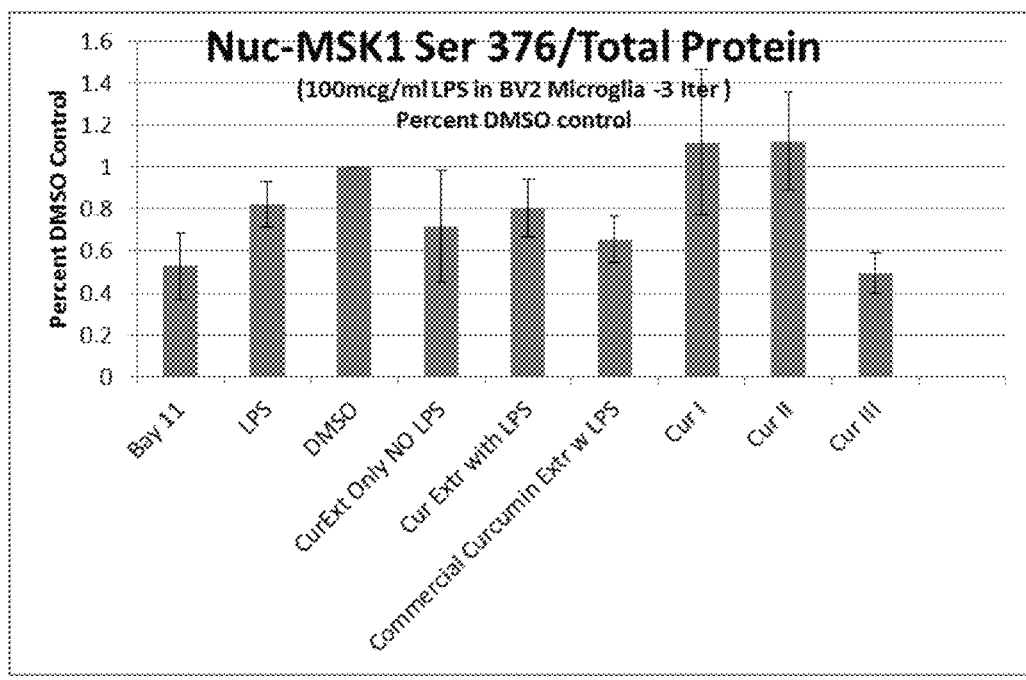
FIG. 10: measurement of nuclear MSK1 that is phosphorylated at the serine 376 phosphosite, relative to total protein concentration in BV2 cell lines provided with curcumin extract, curcuminoid I, curcuminoid II, curcuminoid III, and controls.

Furthermore, and perhaps even more profound, inhibition of MSK1 protein levels was revealed by Western Blot analysis (FIGS. 7 and 8). More specifically, it was found that curcumin III—but not curcumin extract, curcumin I or curcumin II—significantly inhibited and downregulated MSK1 protein levels in both the cytoplasm and the nucleus (FIGS. 7 and 8). The Western Blot analysis summarized in FIGS. 7 and 8 shows curcumin III selectively inhibits MSK1 expression, while certain other curcuminoids (namely, curcumin II) were only shown to inhibit MSK1 serine 376 phosphorylation (FIGS. 9 and 10).

As illustrated in this Example (and in FIGS. 7 and 8), the inventor discovered that curcumin III displays independent and additional pharmacology leading to MSK1 protein downregulation, and that its influence on MSK1 is likely independent and more selectively focused on MSK1 (and not upstream of the kinase). This Example shows the inhibitory influence that is selectively imparted by isolated and enriched curcumin III compositions (and not the other curcuminoids). In addition, the Examples show inhibition of MSK1 expression is not conveyed by typical curcumin extracts—likely because the curcumin III levels in such natural extracts is inherently too low to achieve such activity (a typical natural curcumin extract contains low levels of curcumin III, often about 0.2%-1% curcumin III).

The many aspects and benefits of the invention are apparent from the detailed description, and thus, it is intended for the following claims to cover all such aspects and benefits of the invention which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A method for reducing MSK1 levels in a plurality of cells, which comprises providing to the cells a curcumin composition, wherein at least 5% of the curcumin composition is curcumin III.

2. The method of claim 1, wherein at least 30% of the curcumin composition is curcumin III.

3. The method of claim 2, wherein at least 50% of the curcumin composition is curcumin III.

4. The method of claim 3, wherein at least 70% of the curcumin composition is curcumin III.

5. The method of claim 4, wherein at least 90% of the curcumin composition is curcumin III.

6. The method of claim 5, wherein the curcumin composition is effective to reduce MSK1 levels by at least 25% relative to a control cell line that does not receive the curcumin composition.

7. The method of claim 6, wherein the curcumin composition is effective to reduce MSK1 levels by at least 50% relative to the control cell line.

8. A method for inhibiting MSK1 serine$^{376}$ phosphorylation in a plurality of cells, which comprises providing to the cells a curcumin composition, wherein at least 5% of the curcumin composition is curcumin III.

9. The method of claim 8, wherein at least 30% of the curcumin composition is curcumin III.

10. The method of claim 9, wherein at least 50% of the curcumin composition is curcumin III.

11. The method of claim 10, wherein at least 70% of the curcumin composition is curcumin III.

12. The method of claim 11, wherein at least 90% of the curcumin composition is curcumin III.

13. The method of claim 12, wherein the curcumin composition is effective to reduce MSK1 levels by at least 25% relative to a control cell line that does not receive the curcumin composition.

14. The method of claim 13, wherein the curcumin composition is effective to reduce MSK1 levels by at least 50% relative to the control cell line.

15. A composition that comprises:
(a) a curcumin composition consisting of at least 5% curcumin III;
(b) glucocorticoids; and
(c) a pharmaceutically acceptable solvent, filler, or carrier.

16. The composition of claim 15, wherein the curcumin composition consists of at least 30% curcumin III.

17. The composition of claim 16, wherein the curcumin composition consists of at least 50% curcumin III.

18. The composition of claim 17, wherein the curcumin composition consists of at least 70% curcumin III.

19. The composition of claim 18, wherein the curcumin composition consists of at least 90% curcumin III.

* * * * *